United States Patent
Bean (10) Patent No.: US 12,290,461 B2
(45) Date of Patent: May 6, 2025

(54) EXTERNAL ANKLE BRACE

(71) Applicant: TayCo Brace, Inc., South Bend, IN (US)

(72) Inventor: Mike W. Bean, South Bend, IN (US)

(73) Assignee: TayCo Brace, Inc., South Bend, IN (US)

( * ) Notice: Subject to any disclaimer, the term of this patent is extended or adjusted under 35 U.S.C. 154(b) by 0 days.

(21) Appl. No.: 17/398,599

(22) Filed: Aug. 10, 2021

(65) Prior Publication Data

US 2021/0361458 A1 Nov. 25, 2021

Related U.S. Application Data

(63) Continuation of application No. 15/074,339, filed on Mar. 18, 2016, now abandoned.

(60) Provisional application No. 62/135,823, filed on Mar. 20, 2015.

(51) Int. Cl.
*A61F 5/01* (2006.01)

(52) U.S. Cl.
CPC .................. *A61F 5/0127* (2013.01)

(58) Field of Classification Search
CPC ........ A61F 5/0127; A61F 5/0102; A61F 5/01; A61F 5/0195; A61F 5/0585
See application file for complete search history.

(56) References Cited

U.S. PATENT DOCUMENTS

| | | | |
|---|---|---|---|
| 1,692,896 A | 11/1928 | Hilgert | |
| 4,320,748 A | 3/1982 | Racette et al. | |
| 4,510,927 A | 4/1985 | Peters | |
| 4,517,968 A | 5/1985 | Greene et al. | |
| 4,611,414 A | 9/1986 | Vogel | |
| 4,771,768 A | 9/1988 | Crispin | |
| 4,834,078 A | 5/1989 | Biedermann | |
| 5,031,607 A | 7/1991 | Peters | |
| 5,069,202 A | 12/1991 | Prock | |
| 5,094,232 A | 3/1992 | Harris et al. | |
| 5,429,588 A | 7/1995 | Young et al. | |

(Continued)

OTHER PUBLICATIONS

Martin Alfuth et al., "Biomechanical Comparison of 3 Ankle Braces With and Without Free Rotation in the Sagittal Plane," Journal of Athletic Training, Oct. 2014, pp. 608-616, vol. 49, No. 5.

(Continued)

*Primary Examiner* — Victoria Hicks Fisher
(74) *Attorney, Agent, or Firm* — Pilloff Passino & Cosenza LLP; Martin J. Cosenza (57) ABSTRACT

An, apparatus, including an external gauntlet ankle/foot orthosis configured for application over a shoe configured to provide ankle and foot stability at least one of prophylactically or following trauma, wherein the orthosis includes a first structural section including sub-portions respectively coinciding with an outer portion of a foot and ankle and an inner portion of the foot and ankle and a second structural section including sub-portions respectively coinciding with an outer portion of a lower leg and an inner portion of a lower leg, wherein the second structural section is attached to the first structural section via a plurality of ankle joints, and a first ankle joint of the plurality of ankle joints is configured to accommodate medial malleolus anatomical positioning.

24 Claims, 6 Drawing Sheets

(56) References Cited

U.S. PATENT DOCUMENTS

| | | | |
|---|---|---|---|
| 5,454,173 | A | 10/1995 | Falguere et al. |
| 5,571,078 | A | 11/1996 | Malewicz |
| 5,676,642 | A * | 10/1997 | Peters ................. A61F 5/34 |
| | | | 602/23 |
| 5,792,087 | A | 8/1998 | Pringle |
| 5,921,945 | A | 7/1999 | Gray |
| 5,992,057 | A | 11/1999 | Monti |
| 6,053,884 | A | 4/2000 | Peters |
| 6,299,587 | B1 * | 10/2001 | Birmingham ......... A61F 5/0127 |
| | | | 602/5 |
| 6,409,695 | B1 | 6/2002 | Connelly |
| 6,669,659 | B2 * | 12/2003 | Dittmer ............... A61F 5/05841 |
| | | | 602/5 |
| 6,689,081 | B2 | 2/2004 | Bowman |
| 6,860,864 | B2 * | 3/2005 | Meyer .................. A61F 5/0111 |
| | | | 128/882 |
| 7,127,836 | B1 | 10/2006 | Jamison |
| 7,624,519 | B1 | 12/2009 | Thorne |
| 7,785,283 | B1 | 8/2010 | Bledsoe |
| 9,259,343 | B2 | 2/2016 | Newman |
| 9,844,455 | B2 | 12/2017 | Bradshaw |
| 2001/0051780 | A1 | 12/2001 | Birmingham |
| 2004/0015112 | A1 | 1/2004 | Salutterback et al. |
| 2004/0034316 | A1 | 2/2004 | Castro |
| 2004/0215123 | A1 * | 10/2004 | Slautterback ......... A61F 5/0111 |
| | | | 602/23 |
| 2004/0225241 | A1 | 11/2004 | Scheinberg et al. |
| 2009/0287127 | A1 | 11/2009 | Hu et al. |
| 2010/0137770 | A1 | 6/2010 | Ingmundarson et al. |
| 2011/0173841 | A1 | 7/2011 | McDuff |
| 2012/0145167 | A1 | 6/2012 | Davis |
| 2013/0226059 | A1 | 8/2013 | Morris |
| 2014/0066829 | A1 | 3/2014 | Drillio |
| 2015/0088044 | A1 | 3/2015 | Walborn et al. |
| 2015/0216703 | A1 * | 8/2015 | Madden ................ A61F 5/0127 |
| | | | 602/7 |
| 2015/0313743 | A1 | 11/2015 | Ostergard |
| 2016/0029743 | A1 | 2/2016 | Cavaliere et al. |
| 2016/0235578 | A1 | 8/2016 | Romo et al. |
| 2016/0270944 | A1 | 9/2016 | Bean |

OTHER PUBLICATIONS

Patria A. Hume et al., "Effectiveness of External Ankle Support, Bracing and Taping in Rugby Union," Sports Medicine, May 1998, pp. 285-312, vol. 25, No. 5.

The Free Dictionary by Farlex, "plastically," https://www.thefreedictionary.com/plastically.

* cited by examiner

EXTERNAL ANKLE BRACE

CROSS-REFERENCE TO RELATED APPLICATIONS

This application is a Continuation of U.S. patent application Ser. No. 15/074,339, filed Mar. 18, 2016, Naming Mike W. Bean as an inventor, which claims the benefit of U.S. Provisional Patent Application Ser. No. 62/135,823, which was filed on Mar. 20, 2015, the entirety of which is hereby incorporated by reference for all purposes.

BACKGROUND

Field

The disclosure pertains generally to preventative and rehabilitative equipment, and more particularly to an ankle brace.

Description of Related Art

In the world of sports, ankle injuries are among the most common cause of lost playing time in a sporting career, with a typical ankle injury leaving the athlete out of competition for up to a month. Ankle sprains occur when there is a rapid shifting of weight from one direction to another. The force generated from the movement causes the foot to roll either inwards, which is known as inversion rotation; or outwards, which is known as eversion rotation. Both the inversion and eversion motion of the ankle cause the ligaments on the outside of the ankle to stretch or tear depending on the force that was generated during the movement.

Current braces vary from woven fabric that acts as a glove and wraps around the ankle, to rigid plastic uprights that are strapped around the ankle. The woven fabric braces typically are made of a thin fabric that envelope the ankle and are laced together to support the ankle from both inversion and eversion rotation. The main drawback with these types of braces is that the material lacks the resistance to prevent the ankle from rolling under intense forces. Further, fabric braces also have to be worn within the shoe, which causes the shoe to fit tighter or, in some cases, forces the user to move up a shoe size in order to wear the brace. In terms of the rigid uprights braces, these braces are typically much heavier than the fabric braces and also much larger. Fitting a rigid brace into a tight shoe almost never works, which forces the user to move up to the next shoe size to accommodate for the bulkiness of the brace. When the user moves up a shoe size, the shoe is no longer sized correctly for the foot and thus loses a portion of its intended use and purpose. These braces leave the user at risk for further injury because either the brace isn't strong enough to support the ankle or the shoe isn't fitted properly to the foot.

SUMMARY

The present device overcomes the disadvantages in the related art in an ankle foot orthotic. The device is an external ankle brace for restricting movement of an ankle in a first direction and permitting movement of the ankle in a second direction, wherein the external ankle brace is disposed on the exterior of a shoe. The shoe has a heel portion, a sole, and oppositely disposed sides. The external ankle brace generally includes a rigid heel enclosure, a lateral upright extension, a medial upright extension, where the upright extensions are pivotally connected to the rigid heel enclosure, and the device lastly includes two fastening systems to secure both sides of the heel enclosure together and to secure the external ankle brace to the shoe. The rigid heel enclosure includes a rear portion and a forward portion. The rear portion is for receiving the heel of the shoe. The forward portion further includes a medial sidewall and a lateral sidewall and is for surrounding the sides of the shoe. The lateral upright extension and the medial upright extension are perpendicular to the rigid heel enclosure and pivotally attached to each respective sidewall. The lower fastening system includes at least one connecting strap for connecting the lateral sidewall to the medial sidewall underneath the sole of the shoe. The upper fastening system includes at least one connecting strap for removably connecting the lateral sidewall to the medial sidewall across the top of the shoe.

The external ankle brace further includes a lateral ankle joint that pivotally connects the lateral upright extension to the lateral sidewall and allows the lateral upright extension to move in the second direction relative to the rigid heel enclosure.

Together, the lateral ankle joint, the lateral upright extension, and the rigid heel enclosure prevent movement of the ankle in the first direction.

Additionally, the external ankle brace further includes a medial ankle joint that pivotally connects the medial upright extension to the medial sidewall and allows the medial upright extension to move in the second direction relative to the rigid heel enclosure.

Together, the medial ankle joint, the medial upright extension, and the rigid heel enclosure prevent movement in the first direction.

Furthermore, the rigid heel enclosure includes oppositely disposed upper and lower ends, where the medial ankle joint is positioned closer to the upper end than the position of the lateral ankle joint.

Lastly, the external ankle brace further comprises an upright fastening system which includes at least one connecting strap for removably connecting the lateral upright extension to the medial upright extension above the ankle.

BRIEF DESCRIPTION OF THE DRAWINGS

These and other features, aspects, and advantages of the present disclosure will become better understood when the following detailed description is read with reference to the accompanying drawings in which like numerals are used to indicate like structure throughout the various figures.

DETAILED DESCRIPTION

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

Ankle injuries are among the most common cause of lost playing time in a sporting career and although there are current preventative solutions, those current braces leave the user at risk for further injury because either the brace isn't strong enough to support the ankle or the shoe isn't fitted properly to the foot since "inside the shoe" braces tend to force the user to use a bigger shoe size. The present disclosure provides a rigid support and a much faster application time, all without compromising the fit of the shoe.

Figure 1:
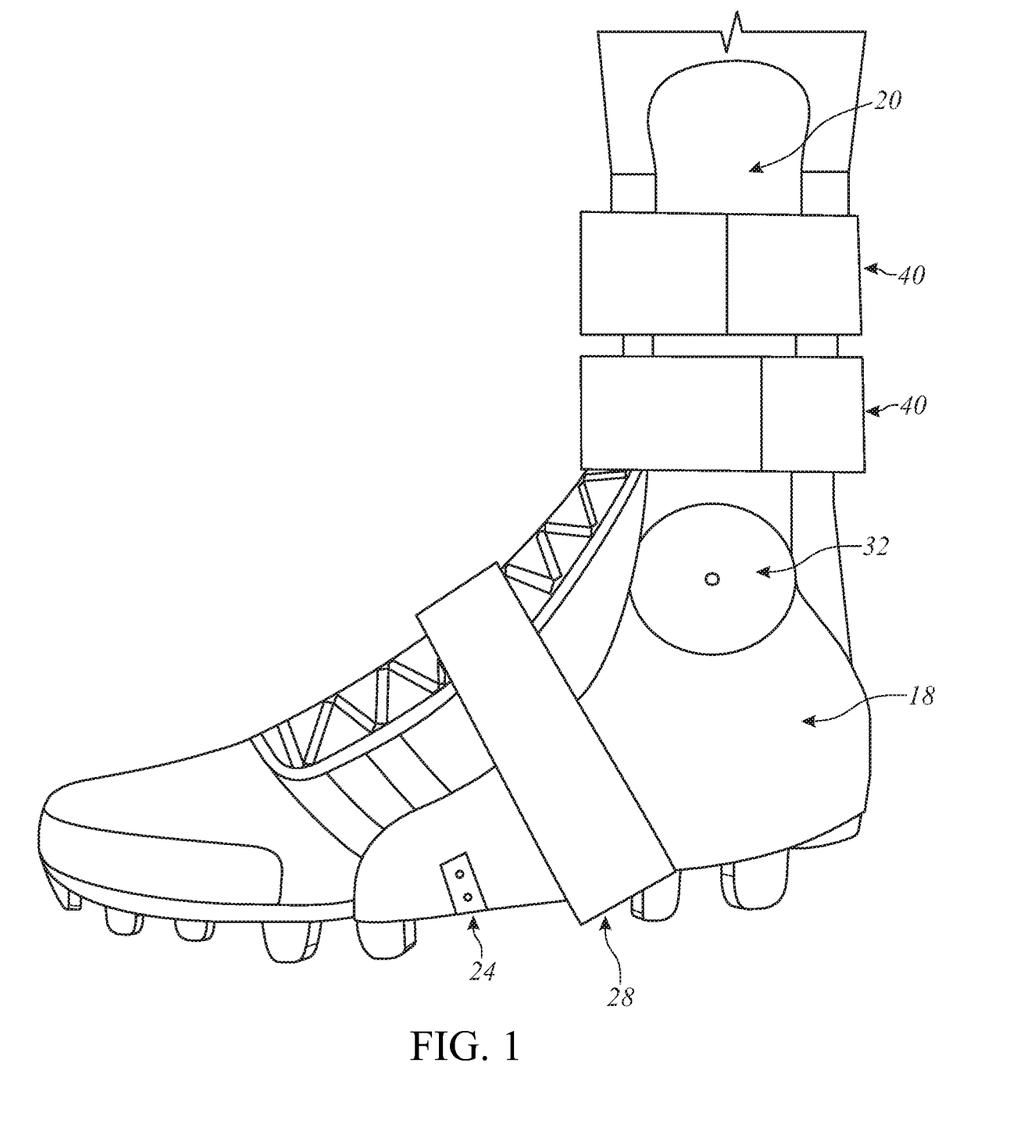
FIG. 1 is a lateral side view showing the external ankle brace with an athletic shoe.

The present disclosure relates to an external ankle brace that is adapted to fit around a shoe to prevent and minimize injury to an ankle. The shoe having a heel portion, a sole, and oppositely disposed sides. The interaction between the external ankle brace and the shoe can be seen in FIG. 1.

Figure 2:
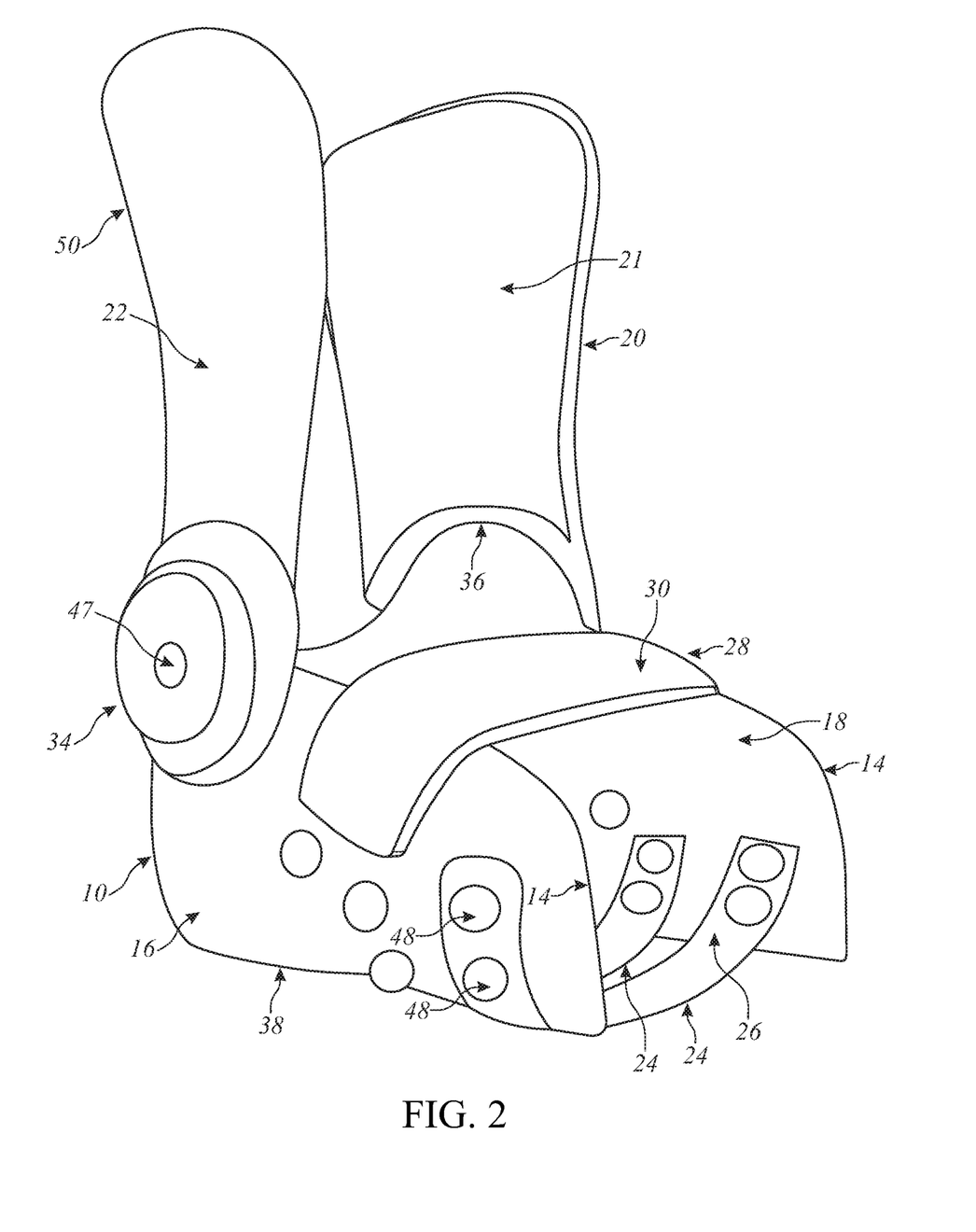
FIG. 2 is a perspective view of the external ankle brace from the medial side.

The external ankle brace of the present disclosure is generally indicated at 50 in FIG. 2. The external ankle brace 50 includes a rigid heel enclosure 10, a lateral upright extension 20, a medial upright extension 22, a lower fastening system 24, and an upper fastening system 28.

Figure 3:
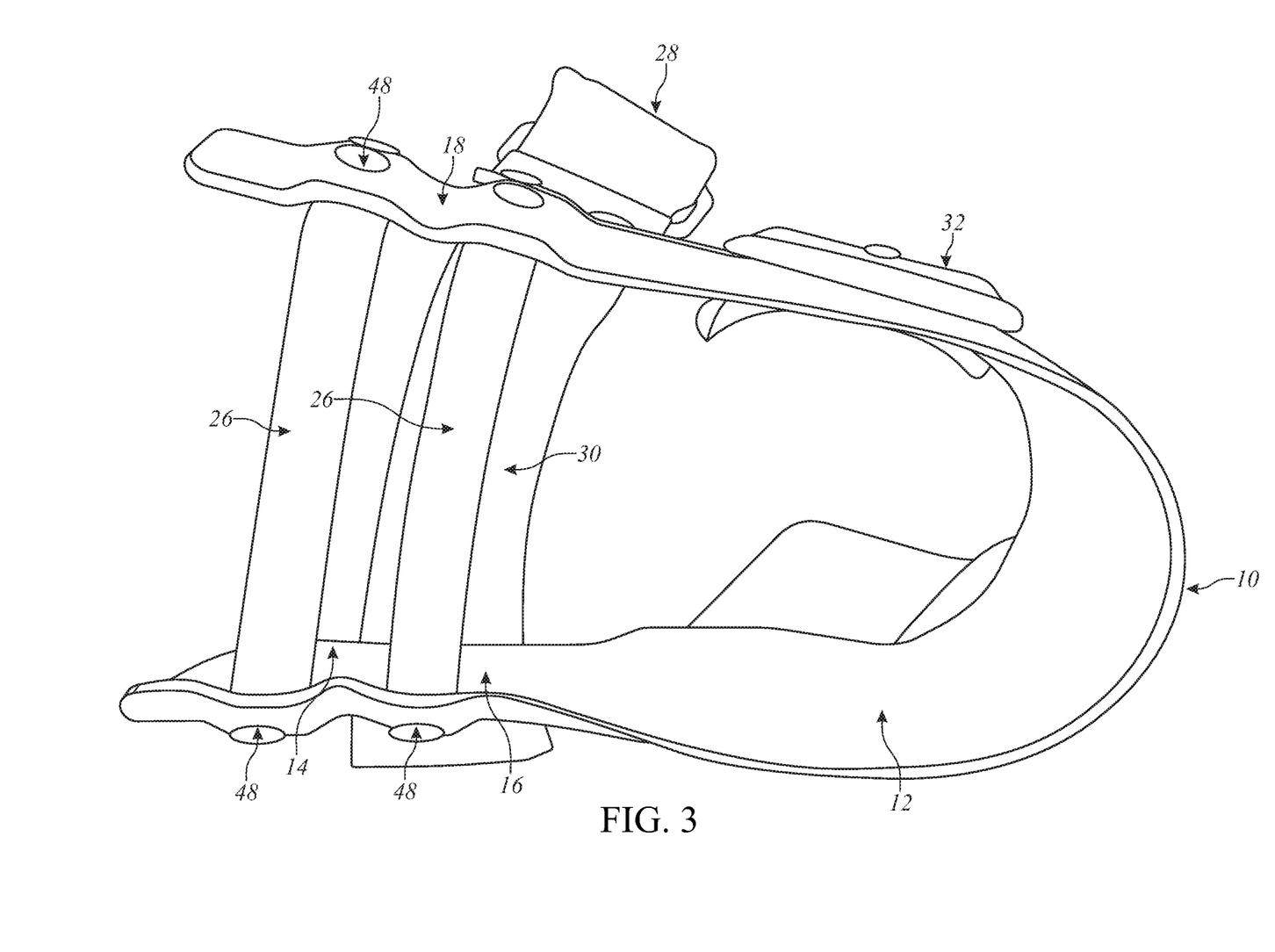
FIG. 3 is a perspective view showing the underside of the external ankle brace.

The rigid heel enclosure 10 has a rear portion 12 (FIG. 3), for receiving the heel of the shoe, and a forward portion 14, for surrounding the sides of the shoe. The heel enclosure 10 may be made from rigid plastic pieces or any other suitable material. The forward portion 14 further includes a medial sidewall 16 and a lateral sidewall 18. The rigid heel enclosure 10 also has an upper end 36 (FIG. 2) for receiving the upright extensions 20 and 22, and a lower end 38 for surrounding the bottom of the shoe.

Figure 4:
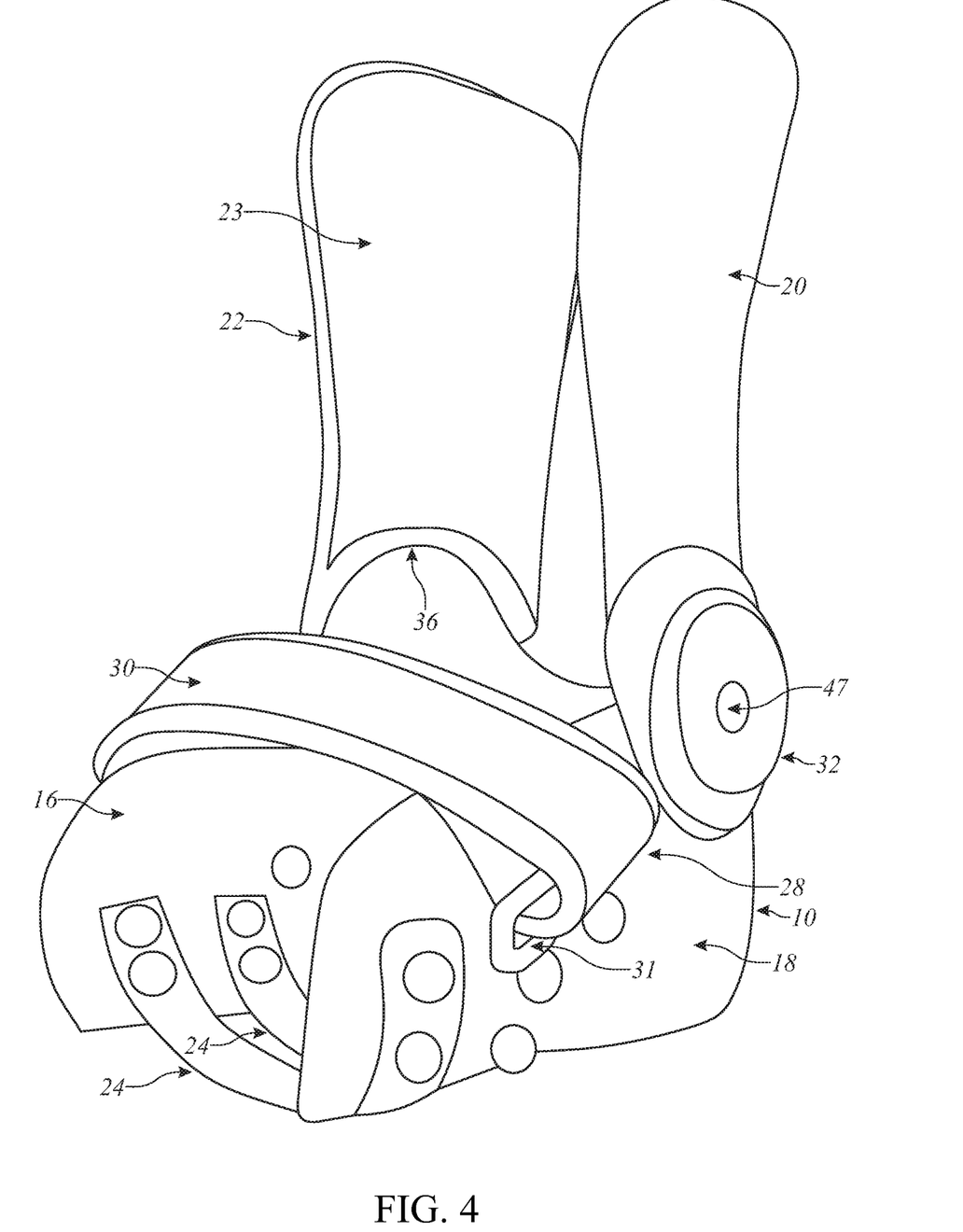
FIG. 4 is a perspective view of the external ankle brace from the lateral side.
Figure 5:
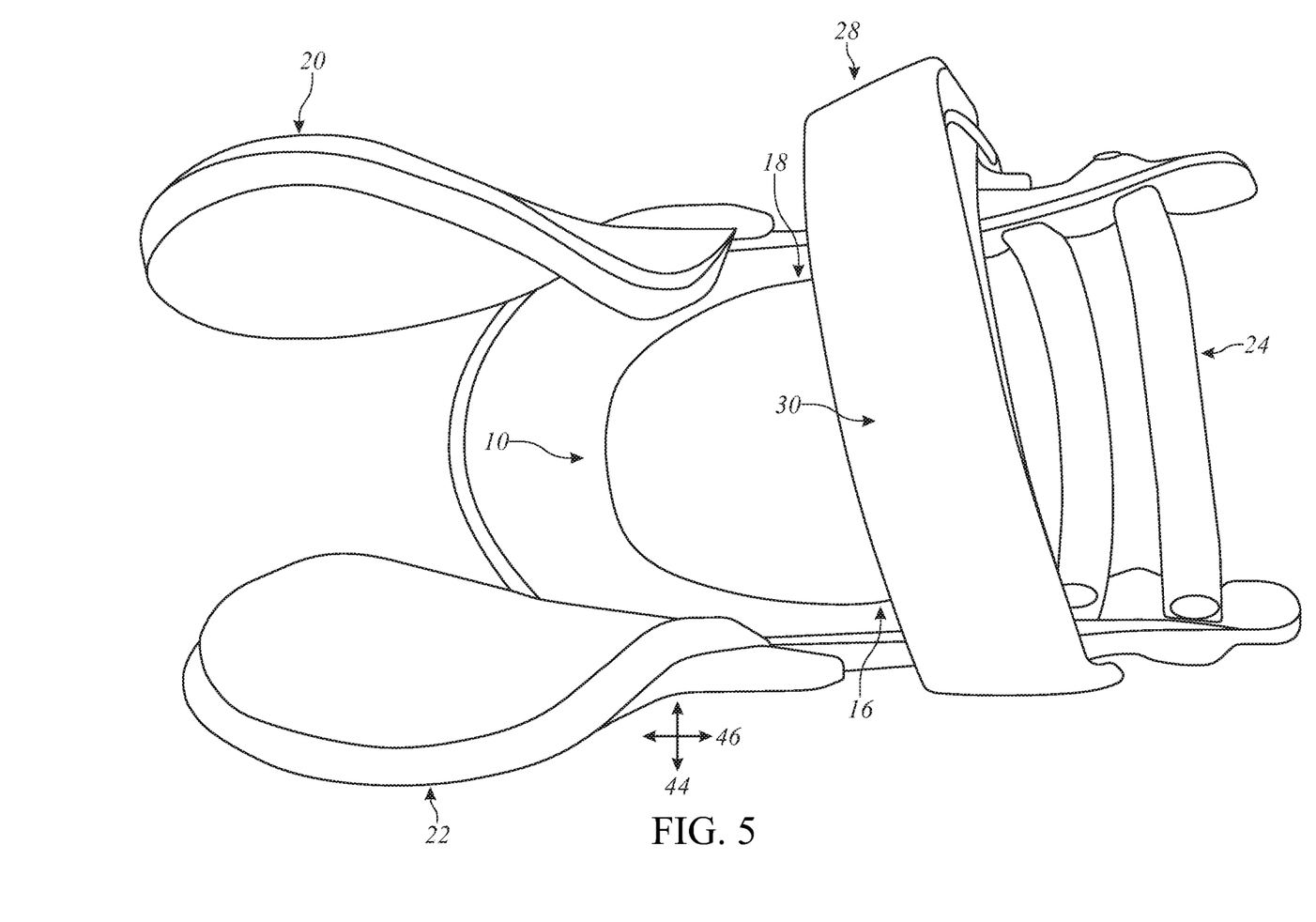
FIG. 5 is a top view of the external ankle brace.
Figure 6:
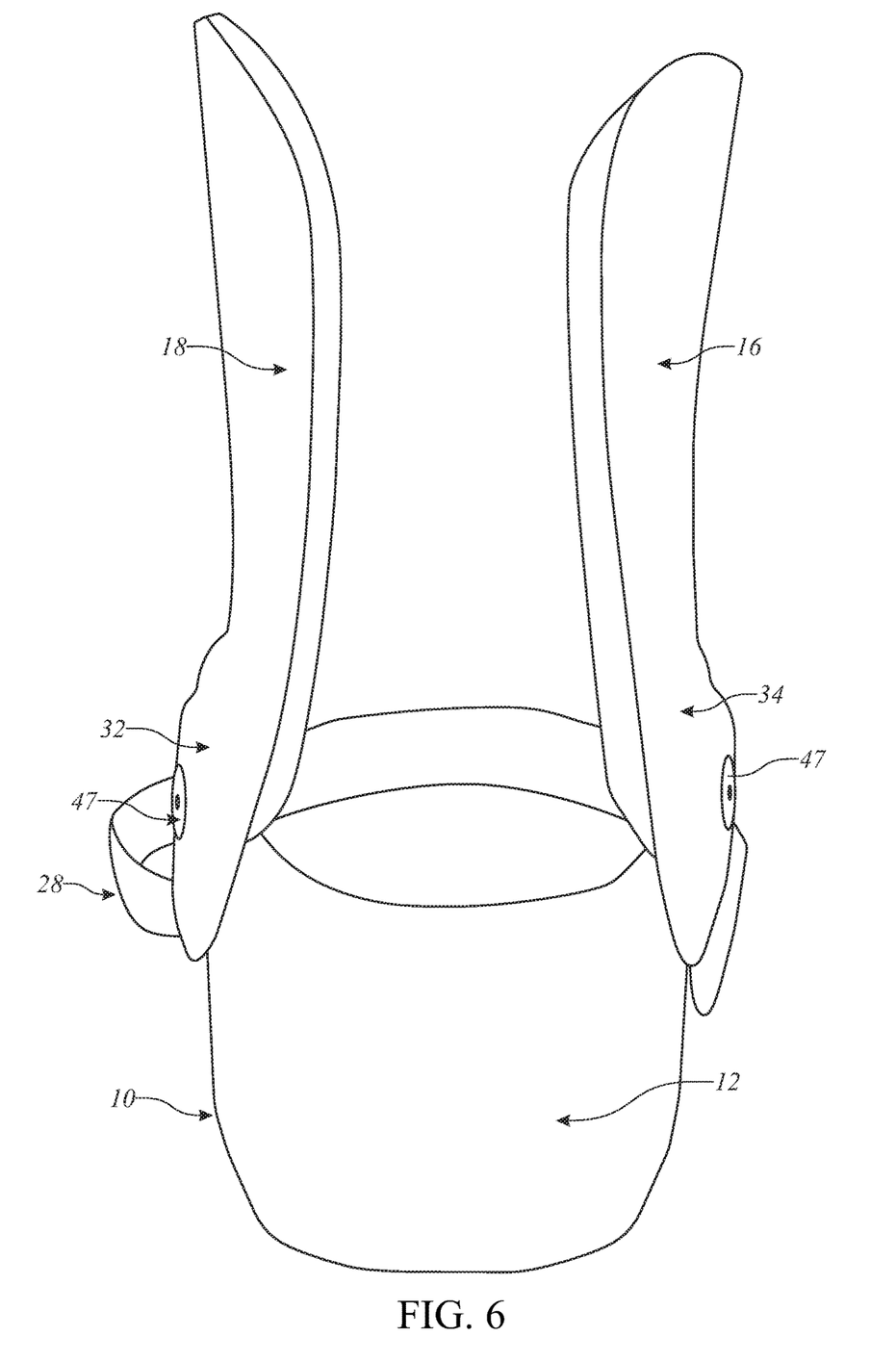
FIG. 6 is a rear view of the external ankle brace.

The lateral upright extension 20 is oriented generally perpendicular to the rigid heel enclosure 10 and is pivotally attached to the lateral sidewall 18 at the upper end 36 by a lateral ankle joint 32 (FIG. 4). The joint allows the lateral upright extension 20 to rotate during motion giving the external ankle brace a less restrictive feel compared to previous braces. The lateral upright extension 20 may be made from plastic or any other suitable material. The lateral ankle joint 32 includes a fastener 47 and allows the lateral upright extension 20 to rotate relative to the lateral sidewall 18. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the lateral upright extension 20 has a concave shape for increased comfort for the user. The lateral upright extension 20 can also include foam padding on the interior side 21 (FIG. 2) of the lateral upright extension 20 to increase comfort and to allow a better fit for the user.

The medial upright extension 22 is perpendicular to the rigid heel enclosure 10 and is pivotally attached to the medial sidewall 16 at the upper end 36 by a medial ankle joint 34. The medial upright extension 22 may be made of rigid plastic or any other suitable material. The medial ankle joint 34 has a fastener 47 and allows the medial upright extension 22 to rotate relative to the medial sidewall 16. To adjust for anatomical positioning of the ankle, the medial ankle joint 34 is positioned closer to the upper end 36 than the position of the lateral ankle joint 32. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the medial upright extension 22 has a concave shape for increased comfort for the user. The medial upright extension 22 can also include foam padding on the interior side 23 (FIG. 4) of the medial upright extension to increase comfort and to allow a better fit for the user.

The lower fastening system 24 has at least one connecting strap 26 and at least one strap fastener 48 for connecting the lateral sidewall 18 to the medial sidewall 16 (FIG. 2) while passing underneath the sole of the shoe. Although the current embodiment uses a rubber strap 26, one having ordinary skill in the art would appreciate that plastic, nylon, or any other suitable strap type that is commonly known in the art could be used. Similarly, although the current embodiment uses rivets 48 to fasten the straps to each of the lateral and medial sidewalls 18 and 16 respectively, any other fastener could be used.

The upper fastening system 28 has at least one connecting strap 30 and at least one strap fastener 48 (FIG. 4) for removably connecting the lateral sidewall 18 to the medial sidewall 16 while passing over the top of the shoe. The upper fastening system further includes a D-ring 31 which is fixed on the lateral sidewall. The Velcro strap 30 is fixed to the medial sidewall and is looped through the D-ring 31 and overlaps back onto the strap 30. This allows for an adjustable fastening system to accommodate various sizes without compromising support. Although the current embodiment uses a Velcro strap 30 to removeably connect the sidewalls 16 and 18, one having ordinary skill in the art would appreciate that any kind of removable and adjustable strap can be used. Similarly, although the current embodiment only uses one connecting strap 30, any number of straps can be used to removeably connect the sidewalls 16 and 18 over the top of the shoe.

As shown in FIG. 5, the external ankle brace 50 restricts movement of the ankle in the first directions indicated by arrows 44 and permits ankle movement in the second directions indicated by arrows 46.

Another embodiment could include an upright fastening system 40 (FIG. 1), which would have at least one connecting strap for removably connecting the lateral upright extension 20 to the medial upright extension 22 above the ankle. This connecting strap could be Velcro or any other type of strap that would allow for an adjustable and removable connection.

Embodiments include an external gauntlet ankle/foot orthosis which applies over the shoe providing ankle and foot stability prophylactically or following acute or chronic trauma. Embodiments relate to an orthotic that limits or prevents ankle inversion, eversion, dorsiflexion and plantar flexion and well as providing mid foot support.

Embodiments can minimize ankle inversion and eversion during physical activity and/or minimize ankle medial and later rotation during physical activity and/or minimize ankle plantar flexion and dorsiflexion during physical activity and/or provide stability to the mid foot in limiting pronation and supination of the foot.

Embodiments can include a foot/ankle orthotic that includes a lateral sidewall, a medial sidewall, a heel enclosed backing connecting the sidewalls, a lateral upright extension, a medial upright extension and a bottom strapping system connecting sidewalls. The lateral and medial upright extensions are attached to the sidewalls with an overlapping ankle joint off-set to accommodate for medial and lateral malleolus anatomical positioning. The lateral sidewall coincides with the outer or exterior portion of the foot/ankle and the medial sidewall coincides with the inner portion of the foot/ankle. The lateral upright extension coincides with the outer or exterior portion of the lower leg and the medial upright extension coincides with the inner portion of the lower leg. Lateral and medial extension walls are configured to rise above the ankle of the wearer of the orthotic by approximately 8-9 inches (from the bottom of the hinge to the top of the extension walls). When donned by the wearer, lateral and medial side walls also partially wrap over the top or dorsum of the foot leaving a gap of approximately 3 to 4 inches between the sidewalls. The width of the medial and lateral upright extensions is approximately 3-4 inches wide.

A feature of an embodiment is to have the securing mechanism include a hook and loop strap across the dorsal (top) of the foot. This Velcro securing strap is riveted to the in place on both the medial and later side walls. A D ring is utilized on the lateral fixation in which the Velcro strap can be fed through and secured back upon itself. The lateral and medial upright extensions are secured by two removable Velcro straps and D rings. Male component Velcro is adhesively attached to each upright and the female component Velcro strap can connect to the uprights are desired positions for appropriate fitting. As an option, the brace may also be applied with various types of athletic adhesive tape in conjunction with or instead of the Velcro strapping and D ring system.

Another feature of an embodiment is an overlapping ankle joint hinge to allow the ankle to move freely through plantar flexion and dorsiflexion. The overlapping ankle joint is located on the medial and lateral aspects of the gauntlet where the medial and lateral side bodies attach with the medial and lateral uprights respectively. The ankle joint hinge components are off set to produce a more anatomically correct gauntlet for a more fluid mobility.

Foam padding (approximately ¼ inch) is attached to the inside of both the medial and lateral uprights to provide additional comfort and protection for the wearer. The gauntlet is sized so that one size can fit multiple size shoes. A separate gauntlet is needed to accommodate both right and left ankles.

A sheet of vacuum formable thermoplastic large enough to cover the entire mold is cut and placed in an oven to be heated to a formable temperature. These are several types and thicknesses of plastic that may be used for this fabrication including orthotic grade polypropylene, polyethylene, and copolymer.

An embodiment includes an apparatus, comprising an external gauntlet ankle/foot orthosis configured for application over a shoe configured to provide ankle and foot stability at least one of prophylactically or following trauma, wherein the external gauntlet ankle/foot orthosis includes a first structural section including sub-portions respectively coinciding with an outer portion of a foot and ankle and an inner portion of the foot and ankle and a second structural section including sub-portions respectively coinciding with an outer portion of a lower leg and an inner portion of the lower leg, wherein the second structural section is attached to the first structural section via a plurality of ankle joints, and the sub-portions of the first structural section are connected by a connector sub-portion, the connector sub-portion having a height that extends upward at least to a height of respective forward-most portions of the sub-portions.

The innovation has been described in an illustrative manner. It is to be understood that the terminology, which has been used is intended to be in the nature of words of description rather than of limitation. Many modifications and variations of the invention are possible in light of the above teachings. Therefore, within the scope of the appended claims, the innovation may be practiced other than as specifically described.

In an embodiment, there is an apparatus, comprising:
an external gauntlet ankle/foot orthosis configured for application over a shoe configured to provide ankle and foot stability at least one of prophylactically or following trauma, wherein the external gauntlet ankle/foot orthosis includes:
a first structural section including sub-portions respectively coinciding with an outer portion of a foot and ankle and an inner portion of the foot and ankle; and
a second structural section including sub-portions respectively coinciding with an outer portion of a lower leg and an inner portion of the lower leg, wherein
the second structural section is attached to the first structural section via a plurality of ankle joints,
the sub-portions of the first structural section are connected by a connector sub-portion, the connector sub-portion having a height that extends upward at least to a height of respective forward-most portions of the sub-portions of the first structural section,
a first ankle joint and a second ankle joint of the plurality of ankle joints include respective hinge components, and
the apparatus further comprises a strap connecting the sub-portions of the second structural section and encircling the lower leg when the external gauntlet ankle/foot orthosis is worn by a human and the apparatus further comprises an upper strapping system connecting the sub-portions of the first structure section.

In an embodiment, there is an apparatus, comprising:
an external gauntlet ankle/foot orthosis configured for application over a shoe configured to provide ankle and foot stability at least one of prophylactically or following trauma, wherein the external gauntlet ankle/foot orthosis includes:
a first structural section including sub-portions adapted to respectively coincide with an outer portion of a foot and ankle and an inner portion of the foot and ankle when the external gauntlet ankle/foot orthosis is worn by a human; and
a second structural section including sub-portions adapted to respectively coincide with an outer portion of a lower leg and an inner portion of the lower leg when the external gauntlet ankle/foot orthosis is worn by the human, wherein
the second structural section is attached to the first structural section via a plurality of ankle joints,
the sub-portions of the first structural section are connected by a connector sub-portion, the connector sub-portion having a height that extends upward at least to a height of respective forward-most portions of the sub-portions of the first structural section,
a first ankle joint and a second ankle joint of the plurality of ankle joints include respective hinge components, and the apparatus further comprises a strap connecting the sub-portions of the second structural section and encircling the lower leg when the external gauntlet ankle/foot orthosis is worn by the human and the apparatus further comprises an upper strapping system connecting the sub-portions of the first structure section.

In an embodiment, the first structural section is rigid. In an embodiment, the external gauntlet ankle/foot orthosis is configured so that a first sub-portion of the sub-portions of the second structural section attaches to a first sub-portion of the sub-portions of the first structural section with an overlapping ankle joint to achieve the accommodation for medial malleolus anatomical positioning, the overlapping ankle joint being one of the plurality of ankle joints. In an embodiment, a first sub-portion of the sub-portions of the second structural section and a second sub-portion of the sub-portions of the second structural section attach to the first structural section with respective overlapping ankle joints off-set to accommodate for the medial malleolus anatomical positioning and to accommodate lateral malleolus anatomical positioning, the respective overlapping ankle joints corresponding to the plurality of ankle joints. In an embodiment, the apparatus includes an upper strapping system, wherein a strap of the upper strapping system extends across a top of the foot when worn by the wearer. In an embodiment, the external gauntlet ankle/foot orthosis is configured so that, when donned by a wearer, a first sub-portion and a second sub-portion of the sub-portions of the first structural section partially wrap over a top of the foot leaving a gap. In an embodiment, the gap is approximately 3 to 4 inches between the first sub-portion and the second sub-portion. In an embodiment, widths of the first sub-portion and the second sub-portion are approximately 3 to 4 inches wide, and lengths of the first sub-portion and the second sub-portion extend along a length of the foot. In an embodiment, a first ankle joint and a second ankle joint of the plurality of ankle joints include respective hinge components and the sub-portions of the first structural section are sidewalls.

In an embodiment, a first ankle joint and a second ankle joint of the plurality of ankle joints include respective hinge components and the sub-portions of the first structural section are sidewalls. In an embodiment, a first ankle joint of the plurality of ankle joints is positioned higher than a second ankle joint of the plurality of ankle joints to accommodate anatomical positioning of the ankle. In an embodiment, a first sub-portion and a second sub-portion of the sub-portions of the first structural section are each configured to extend from the connector sub-portion in a longitudinal direction beyond a talus of the foot and towards a toe of the foot when the external gauntlet ankle/foot orthosis is worn by a human, each of the first sub-portion and the second sub-portion being at least partially located adjacent to an instep area of a corresponding medial or lateral side of the shoe when the external gauntlet ankle/foot orthosis is worn by the human worn by the human. In an embodiment, the apparatus further comprises a lower fastening system comprising at least one connecting strap for connecting said first sub-portion to said second sub-portion underneath a sole of the shoe forward of the talus of the foot, the lower fastening system being the only structure connecting the first sub-portion and the second sub-portion underneath the sole of the shoe such that the sole of the shoe underneath a heel of the foot is exposed to ambient space beneath the shoe when the external gauntlet ankle/foot orthosis is worn by the human, and comprises an upper fastening system comprising at least one connecting strap for removably connecting said first sub-portion to said second sub-portion across a top of the shoe.

In an embodiment, the apparatus comprises a lower strapping system connecting the sub-portions of the first structural section. In an embodiment, the upper strapping system comprises a plurality of straps. In an embodiment, the external gauntlet ankle/foot orthosis is configured so that a first ankle joint of the plurality of ankle joints accommodates the medial malleolus anatomical positioning and the external gauntlet ankle/foot orthosis is configured so that a second ankle joint of the plurality of ankle joints is configured to accommodate lateral malleolus anatomical positioning.

What is claimed is:

1. An apparatus, comprising:
an external gauntlet ankle/foot orthosis configured for application over a shoe configured to provide ankle and foot stability at least one of prophylactically or following trauma, wherein the external gauntlet ankle/foot orthosis includes:
a first structural section including sub-portions configured to respectively coincide with an outer portion of a foot and ankle and an inner portion of the foot and ankle; and
a second structural section including sub-portions configured to respectively coincide with an outer portion of a lower leg and an inner portion of the lower leg, wherein
the second structural section is attached to the first structural section via a plurality of ankle joints,
the sub-portions of the first structural section are connected by a connector sub-portion,
the first structural section and the second structural section are made of thermoplastic,
the apparatus further comprises a strap connecting the sub-portions of the second structural section and encircling the lower leg when the external gauntlet ankle/foot orthosis is worn by the human,
a first sub-portion and a second sub-portion of the sub-portions of the first structural section are each configured to extend from the connector sub-portion in a longitudinal direction beyond a talus of the foot and towards a toe of the foot when the external gauntlet ankle/foot orthosis is worn by a human, each of the first sub-portion and the second sub-portion being at least partially located adjacent to an instep area of a corresponding medial or lateral side of the shoe when the external gauntlet ankle/foot orthosis is worn by the human, the apparatus further comprises:
a fastening arrangement comprising at least one connecting strap for connecting said first sub-portion to said second sub-portion underneath a sole of the shoe forward of the talus of the foot, the fastening arrangement being the only structure connecting the first sub-portion and the second sub-portion underneath the sole of the shoe such that the sole of the shoe underneath a heel of the foot is exposed to ambient space beneath the shoe when the external gauntlet ankle/foot orthosis is worn by the human, and the external gauntlet ankle/foot orthosis limits and/or prevents ankle inversion and eversion.

2. The apparatus of claim 1, wherein:
a first ankle joint and a second ankle joint of the plurality of ankle joints include respective hinge components; and
the sub-portions of the first structural section are sidewalls.

3. The apparatus of claim 1, wherein:
the first structural section is rigid.

4. The apparatus of claim 1, wherein:
the external gauntlet ankle/foot orthosis is configured so that a first sub-portion of the sub-portions of the second structural section attaches to the first sub-portion of the sub-portions of the first structural section with an overlapping ankle joint to achieve an accommodation for medial malleolus anatomical positioning, the overlapping ankle joint being one of the plurality of ankle joints.

5. The apparatus of claim 1, wherein:
a first sub-portion of the sub-portions of the second structural section and a second sub-portion of the sub-portions of the second structural section attach to the first structural section with respective overlapping ankle joints off-set to accommodate for medial malleolus anatomical positioning and to accommodate lateral malleolus anatomical positioning, the respective overlapping ankle joints corresponding to the plurality of ankle joints.

6. The apparatus of claim 1, wherein:
the external gauntlet ankle/foot orthosis provides midfoot support.

7. The apparatus of claim 1, wherein:
a first ankle joint of the plurality of ankle joints and a second ankle joint of the plurality of ankle joints include respective hinge components that are offset to produce an anatomically correct external gauntlet ankle/foot orthosis.

8. The apparatus of claim 1, wherein:
the external gauntlet ankle/foot orthosis prevents ankle inversion and/or eversion.

9. The apparatus of claim 1, wherein:
the external gauntlet ankle/foot orthosis is configured so that, when donned by a wearer, the first sub-portion and the second sub-portion of the sub-portions of the first structural section partially wrap over a top of the foot leaving a gap.

10. The apparatus of claim 1, wherein:
connection of the strap to a respective sub-portion of the sub-portions of the second structural section is a removable connection.

11. The apparatus of claim 1, wherein:
the external gauntlet ankle/foot orthosis prevents ankle inversion and eversion.

12. The apparatus of claim 9, wherein:
the gap is 3 to 4 inches between the first sub-portion and the second sub-portion.

13. The apparatus of claim 9, wherein:
lengths of the first sub-portion and the second sub-portion are configured to extend along a length of the foot.

14. The apparatus of claim 1, wherein:
a first sub-portion of the sub-portions of the second structural section and a second sub-portion of the sub-portions of the second structural section attaches to the first structural section with respective ankle joints off-set to accommodate for the medial malleolus anatomical positioning and lateral malleolus anatomical positioning, the respective ankle joints corresponding to the plurality of ankle joints.

15. The apparatus of claim 1, wherein:
the external gauntlet ankle/foot orthosis is configured to accommodate lateral malleolus anatomical positioning.

16. The apparatus of claim 1, wherein:
the sub-portions of the first structural section are sidewalls.

17. The apparatus of claim 1, wherein:
the at least one connecting strap is located between the first sub-portion and the shoe when the apparatus is worn by the wearer and the at least one connecting strap is located between the second sub-portion and the shoe when the apparatus is worn by the wearer.

18. The apparatus of claim 1, wherein:
a first ankle joint of the plurality of ankle joints is positioned higher than a second ankle joint of the plurality of ankle joints to accommodate anatomical positioning of the ankle.

19. The apparatus of claim 1, wherein:
the external gauntlet ankle/foot orthosis is configured to accommodate medial malleolus anatomical positioning.

20. The apparatus of claim 1, wherein:
forward of the talus, the first sub-portion is configured to extend upwards along a side of a shoe coinciding with the foot.

21. The apparatus of claim 1, wherein:
all strap(s) directly or indirectly interfacing with the first structural section are positioned entirely forward of the talus in use.

22. The apparatus of claim 1, wherein:
a first ankle joint of the plurality of ankle joints is positioned higher than a second ankle joint of the plurality of ankle joints to accommodate medial malleolus anatomical positioning.

23. The apparatus of claim 1, wherein:
the external gauntlet ankle/foot orthosis limits and/or prevents dorsiflection and plantar flexion.

24. The apparatus of claim 1, wherein:
the external gauntlet ankle/foot orthosis is configured so that a first ankle joint of the plurality of ankle joints accommodates the medial malleolus anatomical positioning; and
the external gauntlet ankle/foot orthosis is configured so that a second ankle joint of the plurality of ankle joints is configured to accommodate lateral malleolus anatomical positioning.

* * * * *